United States Patent [19]
Rentzea et al.

[11] Patent Number: 4,835,171
[45] Date of Patent: May 30, 1989

[54] VINYLUREAS, AND FUNGICIDES CONTAINING THESE COMPOUNDS

[75] Inventors: Costin Rentzea, Heidelberg; Wolfgang Spiegler, Worms; Walter Himmele, Walldorf; Eberhard Ammermann, Ludwigshafen; Ernst-Heinrich Pommer, Limburgerhof, all of Fed. Rep. of Germany

[73] Assignee: BASF Altiengesellschaft, Ludwigshafen, Fed. Rep. of Germany

[21] Appl. No.: 717,155

[22] Filed: Mar. 28, 1985

[51] Int. Cl.⁴ ............... C07D 249/012; C07D 233/70; A01N 43/653; A01N 43/48
[52] U.S. Cl. .................... 514/383; 514/399; 514/406; 548/262; 548/341; 548/378
[58] Field of Search .............. 548/262, 341, 378; 514/383, 399, 406

[56] References Cited
U.S. PATENT DOCUMENTS 4,139,365 2/1979 Copping et al. ............... 548/341
4,154,945 5/1979 Brookes et al. ............... 548/341

OTHER PUBLICATIONS
Chemical Week, Jun. 21, 1972, p. 46.

Primary Examiner—Glennon H. Hollrah
Assistant Examiner—Patricia L. Morris
Attorney, Agent, or Firm—Keil & Weinkauf

[57] ABSTRACT

Vinylureas of the formula

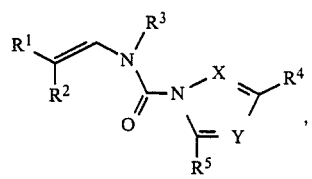

where
$R^1$ and $R^2$ are each hydrogen or an unsubstituted or substituted alkyl or cycloalkyl radical, or
$R^1$ and $R^2$ together form part of an unsubstituted or substituted carbocyclic ring,
$R^3$ is an unsubstituted or substituted alkyl or cycloalkyl radical,
X is nitrogen or C—$R^6$,
Y is nitrogen or CH, and
$R^4$, $R^5$ and $R^6$ are each hydrogen, halogen or alkyl, and fungicides containing these compounds.

4 Claims, No Drawings

VINYLUREAS, AND FUNGICIDES CONTAINING THESE COMPOUNDS

The present invention relates to novel vinyl-azolylureas, processes for their preparation, and fungicides which contain these compounds as active ingredients.

It has been disclosed that N-trichloromethylthiotetrahydrophthalimide can be used as a fungicide in agriculture and in fruit cultivation and horticulture (Chem. Week, June 21st, 1972, page 46). However, the known agent can only be used before infection and, at low application rates, its action does not meet practical requirements.

We have found that vinyl-azolylureas of the formula

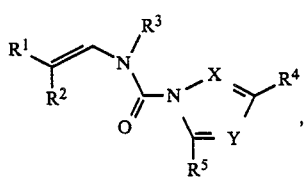

where
$R^1$ and $R^2$ are identical or different and are each hydrogen or alkyl or cycloalkyl, each of which is of not more than 12 carbon atoms and is unsubstituted or substituted by halogen or alkoxy, or
$R^1$ and $R^2$ together form part of a 5-membered or 6-membered carbocyclic ring which is unsubstituted or substituted by one or more alkyl groups of 1 to 3 carbon atoms,
$R^3$ is alkyl or cycloalkyl each of which is of not more than 12 carbon atoms and is unsubstituted or substituted by halogen or alkoxy,
X is nitrogen or C—$R^6$,
Y is nitrogen or CH, one or both of the radicals X and Y being nitrogen, and
$R^4$, $R^5$ and $R^6$ are identical or different and are each hydrogen, halogen or alkyl of not more than 5 carbon atoms, are very effective against harmful fungi.

The novel compounds contain double bonds and may or may not possess chiral centers in the substituents $R^1$, $R^2$ and/or $R^3$, and are generally obtained in the form of Z/E isomer mixtures and, where relevant, as racemates or diastereomer mixtures. For some of the novel compounds, the Z and E isomers can be isolated in pure form, for example by column chromatography or on the basis of solubility differences. Furthermore, pure diastereomers can be converted to pure racemates and enantiomers by conventional methods. All these isomers and their mixtures are embraced by the present invention. Where the compounds according to the invention are used as fungicides, the pure diastereomers, and enantiomers and geometric isomers Z and E, as well as the mixtures of these which are obtained in the synthesis, can be employed. The latter are preferably used.

$R^1$ and $R^2$ are each, for example, hydrogen, methyl, ethyl, propyl, isopropyl, 2-chloropropyl, 3-methoxypropyl, 3-butoxypropyl, butyl, sec.-butyl, isobutyl, tert.-butyl, n-pentyl, 2-methylbutyl, 2,2-dimethylpropyl, n-hexyl, 2,2,3-trimethylpropyl, 3,3-dimethylbutyl, n-heptyl, n-octyl, 2,4,4-trimethylpentyl, 2,2,3,3-tetramethylbutyl, 2-ethylhexyl, n-nonyl, 3,5,5-trimethylhexyl, 2-isopropyl-5-methylhexyl, n-decyl, 3,7-dimethyloctyl, dodecyl, cyclopentyl, cyclohexyl or 4-tert.-butylcyclohexyl, or $R^1$ and $R^2$ together form part of a cyclopentyl or cyclohexyl ring which is unsubstituted or substituted by methyl, ethyl, propyl, isopropyl, n-butyl or tert.-butyl. Alkoxy is, for example, $C_1$–$C_4$-alkoxy.

In formula I, examples of suitable radicals $R^3$ are tert.-butyl, 2-methylbut-2-yl, 2-ethylpent-2-yl, 1,1,2-trimethylprop-1-yl, 1,1-dimethylbut-1-yl, 1,1-dimethylpent-1-yl, 1,1,2,2-tetramethylprop-1-yl, 1-methylcyclopent-1-yl, 1-ethylcyclopent-1-yl, 1-propylcyclopent-1-yl, 1-methylcyclohex-1-yl, 1-ethylcyclohex-1-yl, 1,4-dimethylcyclohex-1-yl, 1-methyl-4-tert.-butylcyclohex-1-yl, 1-ethyl-4-methylcyclohex-1-yl and 1,2,4,6-tetramethylcyclohex-1-yl.

$R^4$, $R^5$ and $R^6$ are each, for example, hydrogen, chlorine, bromine, methyl, ethyl, n-propyl or isopropyl, X is, for example, nitrogen or C—$R^6$, and Y is nitrogen or CH.

The vinylureas of the formula I are obtained by, for example, reacting a compound of the formula

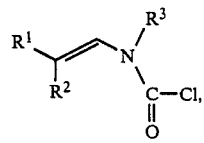

where $R^1$, $R^2$ and $R^3$ have the above meanings,
(a) with the azole of the formula

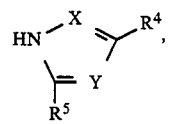

where $R^4$, $R^5$, X and Y have the above meanings, or
(b) with a metal derivative of this, of the formula

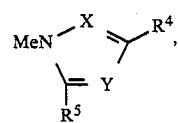

where $R^4$, $R^5$, X and Y have the above meanings and Me is lithium, sodium, potassium or 1 equivalent of calcium, or
(c) with a silyl derivative of this, of the formula

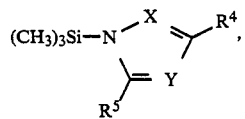

where $R^4$, $R^5$, X and Y have the above meanings.
Reactions (a) and (b) are preferred.

Reaction (a) is carried out in the presence or absence of a solvent or diluent and with or without the addition of an inorganic or organic base and of a reaction accelerator, at from 10° to 120° C.

Examples of preferably used solvents or diluents which are inert to the reactants are aliphatic or aromatic hydrocarbons and halohydrocarbons, such as n-pentane, cyclohexane, methylene chloride 1,1,1-trichloroethane, benzene, toluene, xylene, chlorobenzene, aliphatic ketones, such as acetone, methyl ethyl ketone or diethyl ketone, ethers, such as diethyl ether, methyl tert.-butyl ether, dimethoxyethane, tetrahydrofuran or dioxane, esters, such as ethyl acetate, nitriles, such as acetonitrile, amides, such as dimethylformamide, dimethylacetamide and N-methylpyrrolidone, and mixtures of these.

Examples of suitable bases which, if required, can also be used as acid acceptors in the reaction are alkali metal hydroxides, such as lithium hydroxide, sodium hydroxide, potassium hydroxide or calcium hydroxide, alkali metal carbonates, such as sodium carbonate, potassium carbonate, sodium bicarbonate or potassium bicarbonate, amines, such as triethylamine, tripropylamine, N-methylpyrrolidine, N-methylpiperidine, N,N-dimethylcyclohexylamine, N,N'-tetramethylethylenediamine, N,N-dimethylaniline, N,N-diethylaniline, pyridine or 4-dimethylaminopyridine. However, other conventional bases can also be used.

Preferred reaction accelerators are metal halides, such as sodium iodide or potassium iodide, quaternary ammonium salts, such as tetrabutylammonium chloride, bromide or iodide or benzyltriethylammonium chloride or bromide, and crown ethers, such as 12-crown-4, 15-crown-5, 18-crown-6 or dibenzo-18-crown-6.

Reactions (b) and (c) are carried out in the presence or absence of a solvent or diluent at from 0° to 140° C., preferably from 0° to 100° C. Suitable solvents for these reactions are those which can be used for process (a).

The starting materials of the formula II can readily be prepared by conventional methods, for example by reacting an aliphatic or cycloaliphatic Schiff base with phosgene (German Laid-Open Application No. DOS 1,901,542; cf. also J. P. Chupp, J. Heterocycl. Chem., 8, (1971) 677).

Compounds of the formula I and starting compounds of the formulae IV and V can be prepared using, for example, the following azoles of the formula III: imidazole, 2-methylimidazole, 4(5)-methylimidazole, 2,4-dimethylimidazole, 2,4,5-trimethylimidazole, 4,5-dichloroimidazole, 4,5-dibromoimidazole, 2,4,5-trichloroimidazole, 2,4,5-tribromoimidazole, 2-ethylimidazole, 2-propylimidazole, 2-isopropylimidazole, 2,4-diethylimidazole, pyrazole, 3,5-dimethylpyrazole, 1,2,4-triazole, 3-chloro-1,2,4-triazole, 3,5-dichloro-1,2,4-triazole, 3,5-dibromo-1,2,4-triazole, 3,5-dimethyl-1,2,4-triazole and 1,2,3-triazole.

The Examples which follow illustrate the preparation of the compounds of the formula I:

EXAMPLE 1

20.3 g (0.1 mole) of N-(2-isopropylvinyl)-N-tert.-butylcarbamyl chloride are added dropwise to a solution of 18.1 g (0.22 mole) of 2-methylimidazole in 150 ml of dry tetrahydrofuran at 20° C. The mixture is stirred for 8 hours at 70° C., after which it is cooled to 20° C., the resulting precipitate is filtered off under suction, the filtrate is evaporated down under reduced pressure, the residue is taken up in 200 ml of methylene chloride, the solution is washed with three times 80 ml of water, dried and evaporated down, and the oil which remains is distilled under reduced pressure.

17.2 g of 1-(N-isopropylvinyl-N-tert.-butylcarbamyl)-2-methylimidazole are obtained as a colorless liquid of boiling point 105°–106° C./0.1 mbar and $n_D$ 1.4893 (Compound No. 1).

EXAMPLE 2

21 g (0.103 mole) of N-(2-isopropylvinyl)-N-tert.-butylcarbamyl chloride are added dropwise to a suspension of 10.5 g (0.115 mole) of sodium 1,2,4-triazolide in 100 ml of dry tetrahydrofuran at 20° C. The mixture is stirred for 6 hours at 65° C., after which it is cooled to 20° C., the resulting precipitate is filtered off under suction, the filtrate is evaporated down and the oil which remains is distilled under reduced pressure. 13.6 g of 1-(N-(2-isopropylvinyl)-N-tert.-butylcarbamoyl)-1,2,4-triazole are obtained as a colorless liquid of boiling point 95°–97° C./0.15 mbar and $n_D$ 1.4815 (Compound No. 2)

EXAMPLE 3

27.2 g (0.2 mole) of pyrazole, 1 g of 4-dimethylaminopyridine and 40.6 g (0.2 mole) of N-(2-isopropylvinyl)-N-tert.-butylcarbamyl chloride are added in succession to a suspension of 42 g of potassium carbonate in 150 ml of dry methylene chloride at 20° C. The mixture is stirred for 10 hours at 40° C., after which the resulting precipitate is filtered off under suction and washed with 200 ml of methylene chloride. The filtrate is washed with three times 80 ml of water, dried over $Na_2SO_4$ and evaporated down under reduced pressure, and the oil which remains is evaporated down under reduced pressure. 30.3 g of 1-(N-(2-isopropylvinyl)-N-tert.-butylcarbamyl)-pyrazole are obtained as a colorless liquid of boiling point 104°–105° C./0.3 mbar and $n_D$ 1.4828 (Compound No. 3).

The compounds listed in the table below can be prepared in a similar manner:

| Compound no. | $R^1$ | $R^2$ | $R^3$ | $R^4$ | $R^5$ | X | Y | Physical constants |
| --- | --- | --- | --- | --- | --- | --- | --- | --- |
| 4 | $CH_3$— | H | tert.-butyl | H | H | CH | N | b.p. 90–91° C./0.2 mbar |
| 5 | $C_2H_5$— | H | tert.-butyl | H | H | CH | N | b.p. 90–93° C./0.15 mbar |
| 6 | n-$C_3H_7$— | H | tert.-butyl | H | H | CH | N | b.p. 115–117° C./0.3 mbar |
| 7 | n-$C_4H_9$— | H | tert.-butyl | H | H | CH | N | b.p. 129–131° C./0.4 mbar |
| 8 | n-$C_6H_{13}$— | H | tert.-butyl | H | H | CH | N | b.p. 135–137° C./0.5 mbar |
| 9 | n-$C_6H_{13}$ | H | tert.-butyl | H | H | N | N | b.p. 130–131° C./0.5 mbar |
| 10 | n-$C_{10}H_{21}$ | H | tert.-butyl | H | H | CH | N | b.p.144–146° C./0.4 mbar |
| 11 | n-$C_{10}H_{21}$ | H | tert.-butyl | H | H | N | N | b.p. 141–142° C./0.4 mbar |
| 12 | $(CH_3)_3CCH_2CH(CH_3)CH_2$— | H | tert.-butyl | H | H | CH | N | b.p. 138–140° C./ |

-continued

| Compound no. | R¹ | R² | R³ | R⁴ | R⁵ | X | Y | Physical constants |
|---|---|---|---|---|---|---|---|---|
| 13 | (CH₃)₃CCH₂CH(CH₃)CH₂— | H | tert.-butyl | H | H | N | N | b.p. 134–136° C./0.5 mbar |
| 14 | i-C₃H₇ | H | tert.-butyl | H | C₂H₅— | CH | N | $n_D^{25}$ 1.4870 |
| 15 | i-C₃H₇ | H | tert.-butyl | H | i-C₃H₇— | CH | N | $n_D^{25}$ 1.4859 |
| 16 | i-C₃H₇ | H | tert.-butyl | Cl | H | C—Cl | N | b.p. 130–132° C./0.1 mbar |
| 17 | i-C₃H₇ | H | tert.-butyl | CH₃ | CH₃ | C—CH₃ | N | b.p. 110–113° C./0.1 mbar |
| 18 | i-C₃H₇ | H | tert.-butyl | Cl | H | N | N | m.p. 73–75° C. |
| 19 | i-C₃H₇ | H | tert.-butyl | CH₃ | CH₃ | N | N | b.p. 109–113° C./0.2 mbar |
| 20 | i-C₃H₇ | H | tert.-butyl | CH₃ | CH₃ | N | CH | $n_D^{25}$ 1.4855 |
| 21 | i-C₃H₇ | H | —C(CH₃)₂CH₂CH₃ | H | H | CH | N | $n_D^{25}$ 1.4935 |
| 22 | i-C₃H₇ | H | —C(H₃)₂CH₂CH₃ | H | CH₃ | CH | N | $n_D^{25}$ 1.4924 |
| 23 | i-C₃H₇ | H | —C(CH₃)₂CH₂CH₃ | H | H | N | N | $n_D^{25}$ 1.4850 |
| 24 | i-C₃H₇ | H | —C(CH₃)₂CH₂CH₃ | H | H | N | CH | $n_D^{25}$ 1.4895 |
| 25 | i-C₃H₇ | H | —C(C₂H₅)₃ | H | H | CH | N | m.p. 54–56° C. |
| 26 | i-C₃H₇ | H | —C(C₂H₅)₃ | H | CH₃ | CH | N | b.p. 150–152° C./0.4 mbar |
| 27 | i-C₃H₇ | H | —C(C₂H₅)₃ | H | H | N | N | b.p. 134–136° C./0.4 mbar |
| 28 | i-C₃H₇ | H | —C(C₂H₅)₃ | H | H | N | CH | b.p. 126–128° C./0.5 mbar |
| 29 | i-C₃H₇ | H | —C(CH₃)₂CH(CH₃)₂ | H | H | CH | N | $n_D^{25}$ 1.4970 |
| 30 | i-C₃H₇ | H | —C(CH₃)₂CH(CH₃)₂ | H | H | N | N | $n_D^{25}$ 1.4860 |
| 31 | i-C₃H₇ | H | —C(CH₃)₂CH(CH₃)₂ | H | H | N | CH | $n_D^{25}$ 1.4910 |
| 32 | i-C₃H₇ | H | 1-ethyl-1-cyclohexyl | H | H | CH | N | $n_D^{25}$ 1.5105 |
| 33 | i-C₃H₇ | H | 1-ethyl-1-cyclohexyl | H | H | N | N | $n_D^{25}$ 1.5060 |
| 34 | i-C₃H₇ | H | 1-ethyl-1-cyclohexyl | H | H | N | CH | $n_D^{25}$ 1.5105 |
| 35 | CH₃— | CH₃— | tert.-butyl | H | H | CH | N | b.p. 110–112° C./0.2 mbar |
| 36 | i-C₃H₇— | H | tert.-butyl | H | H | CH | N | b.p. 118–120° C./0.2 mbar |
| 37 | C₂H₅— | C₂H₅— | tert.-butyl | H | H | CH | N | $n_D^{25}$ 1.5030 |
| 38 | C₂H₅— | C₂H₅— | tert.-butyl | H | H | N | N | $n_D^{25}$ 1.4935 |
| 39 | C₂H₅— | C₂H₅— | tert.-butyl | H | H | N | CH | $n_D^{25}$ 1.4930 |
| 40 | —(CH₂)₅— | | tert.-butyl | H | H | CH | N | m.p. 73–76° C. |
| 41 | —(CH₂)₅— | | tert.-butyl | H | H | N | N | m.p. 80–82° C. |
| 42 | —(CH₂)₅— | | tert.-butyl | H | H | N | CH | m.p. 41–43° C. |
| 43 | n-C₄H₉— | C₂H₅ | tert.-butyl | H | H | CH | N | b.p. 144–146° C./0.2 mbar |
| 44 | n-C₄H₉— | C₂H₅ | tert.-butyl | H | H | N | N | b.p. 130–133° C./0.2 mbar |
| 45 | n-C₄H₉— | C₂H₅ | tert.-butyl | H | H | N | CH | b.p. 124–126° C./0.2 mbar |
| 46 | (CH₃)₃CCH₂CH(CH₃)— | H | tert.-butyl | H | H | CH | N | b.p. 148–151° C./0.3 mbar |
| 47 | (CH₃)₃CCH₂CH(CH₃)— | H | tert.-butyl | H | H | N | N | b.p. 135–136° C./0.25 mbar |
| 48 | i-C₃H₇ | H | —C(CH₃)₂C₃H₇—n | H | H | CH | N | $n_D^{25}$ 1.4915 |
| 49 | i-C₃H₇ | H | —C(CH₃)₂C₃H₇—n | H | H | N | N | $n_D^{22}$ 1.4820 |
| 50 | (CH₃)₃CCH₂CH(CH₃)— | H | —C(CH₃)₂C₃H₇—n | H | H | CH | N | $n_D^{22}$ 1.4900 |
| 51 | (CH₃)₃CCH₂CH(CH₃)— | H | —C(CH₃)₂C₃H₇—n | H | H | H | N | $n_D^{22}$ 1.4825 |
| 52 | n-C₁₀H₂₃ | H | tert.-butyl | H | H | CH | N | $n_D^{22}$ 1.4800 |
| 53 | n-C₁₀H₂₃ | H | tert.-butyl | H | H | N | N | $n_D^{22}$ 1.4760 |
| 54 | i-C₃H₇ | H | n-butyl | H | H | N | CH | b.p. 148–152° C./0.4 mbar |
| 55 | i-C₃H₇ | H | n-butyl | H | H | N | N | b.p. 130–140° C./0.35 mbar |
| 56 | i-C₃H₇ | H | n-hexyl | H | H | CH | N | $n_D^{22}$ 1.5029 |
| 57 | i-C₃H₇ | H | n-hexyl | H | H | N | N | $n_D^{22}$ 1.4970 |

The novel compounds have an excellent action on a broad spectrum of plant-pathogenic fungi, especially from the Ascomycetes and Basidiomycetes classes. Some of them have a systemic action and may be used as soil and foliar fungicides. They may also be used for protecting materials, e.g., for combatting wood-destroying fungi such as *Coniophora puteana* and *Polystictus versicolor*.

The fungicidal compounds are of particular interest for combatting a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combatting the following diseases: *Pseudocercosporella herpotrichoides* in cereals, *Erysiphe graminis* in cereals, *Erysiphe cichoracearum* in Cucurbitaceae, *Podosphaera leucotricha* in apples, *Uncinula necator* in grapes, *Puccinia* species in cereals, *Rhizoctonia solani* in cotton, *Ustilago* species in cereals and sugarcane, *Venturia inaequalis* (apple scab), *Septoria nodorum* in wheat, *Botrytis cinerea* in grapes and strawberries, *Rhynchosporium secalis* and *Pyrenophora teres* in cereals, *Alternaria solani* in tomatoes, and *Pyricularia oryzae* in rice.

The active ingredients may suppress, simultaneously, the growth of two or more of the said fungi, and are well tolerated by crop plants. Some of the active ingredients have curative properties i.e., the agents may be applied after plant infection by the pathogen, and success is still ensured.

The fungicidal agents generaly contain from 0.1 to 95, preferably from 0.5 to 90, wt% of active ingredient.

The application rates depend on the effect desired, and range from 0.1 to 5 kg of active ingredient per hectare.

The novel active ingredients may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur, i.e., the fungicidal action of the combination product is greater than the effect of the individual components added together. Examples of fungicides which can be combined with the novel compounds are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimthylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxy-carbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenylsulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiyne-4,4-dioxide
2,3-dihydro-5-carboxanilido-6-methyl-1,4-oxathiyne
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazolylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidine-methanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene and various fungicides, such as dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-(ethylaminocarbonyl)-2-methoximino)-acetamide
1-(2-(2,4-dichlorophenyl)-pentyl-1H-1,2,4-triazole
2,4-difluoro-alpha-(1H-1,2,4-triazolyl-1-ylmethyl)-benzhydryl alcohol The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be sprayed direct or to be used after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalene-sulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of formulations are given below.

I. 90 parts by weight of compound 4 is mixed with 10 parts by weight of N-methyl-alpha-pyrrolidone. A mixture is obtained which is suitable for application in the form of very fine drops.

II. 20 parts by weight of compound 18 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 21 is dissolved in a mixture consisting of 30 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound 22 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of compound 25 is well mixed with 3 parts by weight of the sodium salt of diisobutyl-naphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of compound 29 is intimately mixed with 95 parts by weight of particulate kaolin. A dust is obtained containing 5% by weight of the active ingredient.

VII. 30 parts by weight of compound 32 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 36 is intimately mixed with 30 parts of the sodium salt of a phenolsulfonic acid-urea-formaldehyde condensate, 2 parts of silica gel and 48 parts of water to give a stable aqueous dispersion.

IX. 20 parts of compound 21 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds. Comparative agent A is the prior art active ingredient N-trichloromethylthiotetrahydrophthalimide (Chem. Week, June 21, 1972, p. 46), which is particularly suitable for combatting Botrytis.

EXPERIMENT 1

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea,* and placed at 22° to 24° C. in a chamber of high humidity. After 5 days, the disease has spread to such a great extent on the untreated plants that the necroses covered the major portion of the leaves.

The results of this experiment show that, on application of, for example, 0.05% spray liquors, active ingredient 21 had a better fungicidal action (e.g., 90%) than prior art compound A (e.g., 70%).

EXPERIMENT 2

Action on cucumber mildew

The leaves of pot-grown cucumber seedlings of the "Chinesische Schlange" variety were sprayed at the 2-leaf stage with a spore suspension of cucumber mildew (*Erysiphe cichoracearum*). After about 20 hours, the plants were sprayed to runoff with aqueous emulsions consisting (dry basis) of 80% of active ingredient and 20% of emulsifier. After the sprayed-on layer had dried, the plants were set up in the greenhouse at from 20° to 22° C. and a relative humidity of 70 to 80%. To assess the action of the novel compounds, the extent of fungus spread was determined after 8 days.

The results of this experiment show that novel active ingredients 4, 21, 22, 25, 29, 32 and 36, applied as 0.025% spray liquors, had a good fungicidal action (e.g., 100%).

EXPERIMENT 3

Action on *Pyricularia oryzae*

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae.*

The plants were then set up in controlled-climate cabinets at 22° to 24° C. and 95 to 99% relative humidity. The extent of fungus attack was determined after 6 days.

The results of the experiment show the active ingredient 18, applied for instance as a 0.05% spray liquor, had a good fungicidal action (e.g., 90%).

We claim:

1. A vinylurea of the formula

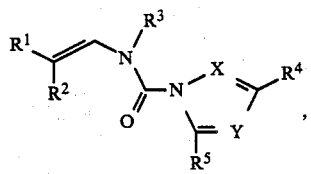

where
$R^1$ is unsubstituted or halogen or $C_1-C_4$-alkoxy substituted alkyl or cycloalkyl, each of which alkyl or cycloalkyl contains not more than 12 carbon atoms apart from its alkoxy substituents,
$R^2$ is hydrogen or unsubstituted or halogen or $C_1-C_4$-alkoxy substituted cycloalkyl of not more than 12 ring carbon atoms or
$R^1$ and $R^2$ together with the carbon to which they both are attached form a 5-membered or 6-membered saturated carbocyclic ring which is unsubstituted or substituted by one or more alkyl groups of 1 to 3 carbon atoms, $R^3$ is alkyl of not more than 12 carbon atoms which further may contain halogen substituents,
X is nitrogen or $C-R^6$,
Y is nitrogen or CH, one or both of the radicals X and Y being nitrogen, and
$R^4$, $R^5$ and $R^6$ are identical or different and each is hydrogen, halogen or alkyl of not more than 5 carbon atoms.

2. A vinylurea of the formula I as set forth in claim 1, where $R^1$ and $R^2$ are methyl, ethyl, propyl, isopropyl, butyl, sec.-butyl, isobutyl, tert.-butyl, n-pentyl, 2-methylbutyl, 2,2-dimethylpropyl, n-hexyl, 2,2,3-trimethylpropyl, 3,3,-dimethylbutyl, n-heptyl, n-octyl, 2,4,4-trimethylpentyl, 2,2,3,3-tetramethylbutyl, 2-ethylhexyl, n-nonyl, 3,5,5-trimethylhexyl, 2-isopropyl-5-methylhexyl, n-decyl, 3,7-dimethyloctyl, or dodecyl, $R^2$ can also be H, or $R^1$ and $R^2$ together form part of a cyclopentyl or cyclohexyl ring which is unsubstituted or substituted by methyl, ethyl, propyl, isopropyl, n-butyl or tert.-butyl, $R^3$ is tert.-butyl, 2-methylbut-2-yl, 2-ethyl-pent-2-yl, 1,1,2-trimethylprop-1-yl, 1,1-dimethylbut-1-yl, 1,1-dimethylpent-1-yl, 1,1,2,2-tetramethylprop-1-yl, 1-methylcyclopenty-1-yl, 1-ethylcyclopent-1-yl, 1-propylcyclopent-1-yl, and $R^4$, $R^5$ and $R^6$ are each hydrogen, chlorine, bromine, methyl, ethyl, n-propyl or isopropyl, X is nitrogen or $C-R^6$, and Y is nitrogen or CH.

3. A process for combatting fungi, wherein the fungi or the materials, areas, plants or seed threatened by fungus attack are treated with a fungicidally effective amount of a vinylurea of the formula

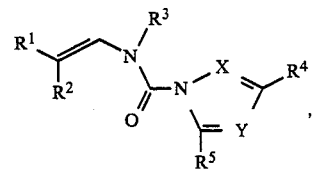

where
$R^1$ and $R^2$ are identical or different and are each unsubstituted or halogen or $C_1-C_4$-alkoxy substituted alkyl or cycloalkyl, each of which when unsubstituted is not more than 12 carbon atoms, $R^2$ can also be H, or
$R^1$ and $R^2$ together with the carbon to which they both are attached form a 5-membered or 6-membered saturated carbocyclic ring which is unsubstituted or substituted by one or more alkyl groups of 1 to 3 carbon atoms,
$R^3$ is alkyl or cycloalkyl each of which is of not more than 12 carbon atoms and which further may contain halogen substituents,
X is nitrogen or $C-R^6$,
Y is nitrogen or CH, one or both of the radicals X and Y being nitrogen, and
$R^4$, $R^5$ and $R^6$ are identical or different and are each hydrogen, halogen or alkyl of not more than 5 carbon atoms.

4. A fungicidal agent containing an inert additive and an effective amount of vinylurea of the formula

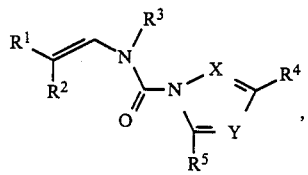

where $R^1$ and $R^2$ are identical or different and are each alkyl or cycloalkyl, each of which is not more than 12 carbon atoms and which further may contain halogen or $C_1$–$C_4$-alkoxy substituents, or $R^2$ can also be H, or $R^1$ and $R^2$ together form with the carbon to which they both are attached a 5-membered or 6-membered saturated carbocyclic ring which is unsubstituted or substituted by one or more alkyl groups of 1 to 3 carbon atoms, $R^3$ is alkyl of not more than 12 carbon atoms and which further may contain halogen substituents, X is nitrogen or C—$R^6$, Y is nitrogen or CH, one or both of the radicals X and Y being nitrogen, and $R^4$, $R^5$ and $R^6$ are identical or different and are each hydrogen, halogen or alkyl of not more than 5 carbon atoms.

* * * * *

UNITED STATES PATENT AND TRADEMARK OFFICE
CERTIFICATE OF CORRECTION

PATENT NO. : 4,835,171

DATED : May 30, 1989

INVENTOR(S) : Costin RENTZEA, et al.

It is certified that error appears in the above-identified patent and that said Letters Patent is hereby corrected as shown below: Title page:

In the FOREIGN APPLICATION PRIORITY DATA should read: Federal Republic of Germany Application No. P 34 11 388.6
               Filed: March 28, 1984

In the FOREIGN PATENT DOCUMENTS should read: 3,235,050   Fed. Rep. of Germany
                                filed March 22, 1984

Signed and Sealed this

Twenty-third Day of January, 1990

Attest:

JEFFREY M. SAMUELS

Attesting Officer        Acting Commissioner of Patents and Trademarks